US012156994B2

(12) United States Patent
Mosebach et al.

(10) Patent No.: US 12,156,994 B2
(45) Date of Patent: *Dec. 3, 2024

(54) DRUG DELIVERY DEVICE

(71) Applicant: SANOFI-AVENTIS DEUTSCHLAND GMBH, Frankfurt am Main (DE)

(72) Inventors: Carsten Mosebach, Frankfurt am Main (DE); Thomas Mark Kemp, Ashwell (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 327 days.

This patent is subject to a terminal disclaimer.

(21) Appl. No.: 17/120,670

(22) Filed: Dec. 14, 2020

(65) Prior Publication Data

US 2021/0093790 A1 Apr. 1, 2021

Related U.S. Application Data

(63) Continuation of application No. 15/578,567, filed as application No. PCT/EP2016/062449 on Jun. 2, 2016, now Pat. No. 10,888,668.

(30) Foreign Application Priority Data

Jun. 3, 2015 (EP) .................................... 15170581

(51) Int. Cl.
*A61M 5/315* (2006.01)
*A61M 5/20* (2006.01)
*A61M 5/32* (2006.01)

(52) U.S. Cl.
CPC ........ *A61M 5/3157* (2013.01); *A61M 5/2033* (2013.01); *A61M 5/31578* (2013.01);
(Continued)

(58) Field of Classification Search
CPC .............. A61M 5/3157; A61M 5/2033; A61M 5/3158; A61M 5/31578; A61M 5/3204;
(Continued)

(56) References Cited

U.S. PATENT DOCUMENTS 4,629,454 A 12/1986 Grier
4,693,711 A 9/1987 Bremer et al.
(Continued)

FOREIGN PATENT DOCUMENTS

CN 200987443 12/2007
CN 101107032 1/2008
(Continued)

OTHER PUBLICATIONS

U.S. Appl. No. 16/759,488, filed Apr. 27, 2020, Revellat et al.
(Continued)

*Primary Examiner* — Michael J Tsai
*Assistant Examiner* — Nidah Hussain
(74) *Attorney, Agent, or Firm* — Fish & Richardson P.C.

(57) ABSTRACT

The disclosure relates to a drug delivery device including a plunger disposed within a case and an audible indicator that comprises a resilient element. The plunger is slidable from a proximal position to a distal position within the case and the resilient element is in a first configuration when the plunger is in the proximal position, such that the resilient element is deflected radially outwards to a second configuration during movement of the plunger from the proximal position towards the distal position. The resilient element moves from the second configuration towards the first configuration when the plunger moves towards or reaches the distal position, thereby generating an audible and tactile signal.

22 Claims, 3 Drawing Sheets

(52) U.S. Cl.
CPC ........ *A61M 5/3158* (2013.01); *A61M 5/3204* (2013.01); *A61M 2205/581* (2013.01); *A61M 2205/582* (2013.01)

(58) Field of Classification Search
CPC ...... A61M 2205/581; A61M 2205/582; A61M 5/14232; F04B 43/12
USPC ........................................................ 604/198
See application file for complete search history.

(56) References Cited

U.S. PATENT DOCUMENTS

| | | | |
|---|---|---|---|
| 4,810,249 | A | 3/1989 | Haber et al. |
| 5,114,406 | A | 5/1992 | Gabriel et al. |
| 5,116,313 | A | 5/1992 | McGregor |
| 5,127,906 | A | 7/1992 | Landry et al. |
| 5,271,527 | A * | 12/1993 | Haber ............... A61M 5/31551 222/137 |
| 5,391,157 | A | 2/1995 | Harris et al. |
| 7,611,495 | B1 | 11/2009 | Gianturco |
| 8,979,807 | B2 | 3/2015 | Grunhut et al. |
| 9,168,339 | B2 | 10/2015 | Cowe |
| 9,199,038 | B2 | 12/2015 | Daniel |
| 9,216,251 | B2 | 12/2015 | Daniel |
| 9,744,306 | B2 | 8/2017 | Cowe |
| 9,764,096 | B2 | 9/2017 | Maritan |
| 10,888,668 | B2 * | 1/2021 | Mosebach ......... A61M 5/31578 |
| 10,918,811 | B2 | 2/2021 | Mosebach et al. |
| 10,926,032 | B2 | 2/2021 | Mosebach et al. |
| 11,357,922 | B2 | 6/2022 | Mosebach et al. |
| 11,400,232 | B2 | 8/2022 | Schader et al. |
| 11,654,246 | B2 | 5/2023 | Revellat et al. |
| 2002/0188247 | A1* | 12/2002 | Peery ................ A61M 37/0069 600/7 |
| 2004/0210199 | A1* | 10/2004 | Atterbury ............ G01D 5/2497 604/224 |
| 2005/0027255 | A1 | 2/2005 | Lavi et al. |
| 2005/0038392 | A1 | 2/2005 | DeSalvo |
| 2007/0088248 | A1 | 4/2007 | Glenn et al. |
| 2008/0021373 | A1 | 1/2008 | Rosati |
| 2010/0198182 | A1 | 8/2010 | Lanigan et al. |
| 2011/0026721 | A1 | 2/2011 | Parker |
| 2011/0105952 | A1 | 5/2011 | Bernstein et al. |
| 2011/0238014 | A1 | 9/2011 | Maritan |
| 2013/0023749 | A1 | 1/2013 | Afanasewicz et al. |
| 2013/0090605 | A1* | 4/2013 | O'Connor ......... A61M 5/31525 604/205 |
| 2013/0317427 | A1 | 11/2013 | Brereton et al. |
| 2013/0324925 | A1 | 12/2013 | Brereton et al. |
| 2013/0345642 | A1* | 12/2013 | Cowe ............... A61M 5/31535 604/189 |
| 2014/0114250 | A1 | 4/2014 | DeSalvo et al. |
| 2014/0243751 | A1* | 8/2014 | Brereton ............ A61M 5/3204 604/197 |
| 2014/0276568 | A1 | 9/2014 | Worden et al. |
| 2014/0343527 | A1 | 11/2014 | Scarpine et al. |
| 2015/0265772 | A1 | 9/2015 | Maritan |
| 2015/0320939 | A1* | 11/2015 | Beek ...................... A61M 5/326 604/193 |
| 2016/0008541 | A1* | 1/2016 | Hirschel ............. A61M 5/2033 604/137 |
| 2016/0008542 | A1 | 1/2016 | Hirschel et al. |
| 2016/0015899 | A1 | 1/2016 | Plumptre et al. |
| 2016/0144133 | A1 | 5/2016 | Kemp |
| 2016/0361503 | A1* | 12/2016 | Bendek .................. A61M 5/20 |
| 2017/0136173 | A1 | 5/2017 | Melander et al. |
| 2018/0154078 | A1 | 6/2018 | Mosebach et al. |
| 2018/0154085 | A1 | 6/2018 | Mosebach et al. |
| 2018/0154089 | A1* | 6/2018 | Mosebach ........... A61M 5/3202 |
| 2020/0289764 | A1 | 9/2020 | Revellat et al. |
| 2021/0128837 | A1 | 5/2021 | Mosebach et al. |
| 2021/0170115 | A1 | 6/2021 | Mosebach et al. |
| 2021/0369966 | A1 | 12/2021 | Schader et al. |
| 2022/0257865 | A1 | 8/2022 | Mosebach et al. |
| 2022/0305206 | A1 | 9/2022 | Schader et al. |
| 2023/0277777 | A1 | 9/2023 | Revellat et al. |

FOREIGN PATENT DOCUMENTS

| | | |
|---|---|---|
| CN | 201111673 | 9/2008 |
| CN | 201243374 | 5/2009 |
| CN | 102209564 | 10/2011 |
| CN | 102842236 | 12/2012 |
| CN | 202887394 | 4/2013 |
| CN | 103177716 | 6/2013 |
| CN | 103235538 | 8/2013 |
| CN | 104080499 | 10/2014 |
| CN | 104519929 | 4/2015 |
| CN | 105188809 | 12/2015 |
| CN | 105327432 | 2/2016 |
| CN | 105451792 | 3/2016 |
| CN | 106573114 | 4/2017 |
| DE | 7833454 | 5/1979 |
| DE | 3935672 | 11/1990 |
| EP | 2722065 A1 | 4/2014 |
| EP | 2727617 | 5/2014 |
| EP | 2823841 A1 | 1/2015 |
| EP | 2868338 | 5/2015 |
| EP | 3302632 | 9/2020 |
| JP | H06-190041 | 7/1994 |
| JP | H07-509636 | 10/1995 |
| JP | 2005-508205 | 3/2005 |
| JP | 2011-519712 | 7/2011 |
| JP | 2012-504006 | 2/2012 |
| JP | 2013-526894 | 6/2013 |
| JP | 2013-526904 | 6/2013 |
| JP | 2013-146600 | 8/2013 |
| JP | 2013-534164 | 9/2013 |
| JP | H5-508098 | 5/2014 |
| JP | 2014-526298 | 10/2014 |
| JP | 2014-531961 | 12/2014 |
| JP | 2015-526215 | 9/2015 |
| JP | 2015-536184 | 12/2015 |
| JP | 2016-512766 | 5/2016 |
| JP | 2016-513507 | 5/2016 |
| JP | 2016-526460 | 9/2016 |
| RU | 2140794 | 11/1999 |
| RU | 2012137269 | 3/2014 |
| WO | WO 1992/017223 | 10/1992 |
| WO | WO 1994/003222 | 2/1994 |
| WO | WO 2002/092153 | 11/2002 |
| WO | WO 2005/046773 | 5/2005 |
| WO | WO 2006/079481 | 8/2006 |
| WO | WO 2009/140251 | 11/2009 |
| WO | WO 2010/035057 | 4/2010 |
| WO | WO 2011/079278 | 6/2011 |
| WO | WO 2011/123024 | 10/2011 |
| WO | WO 2012/022810 | 2/2012 |
| WO | WO 2012/045350 | 4/2012 |
| WO | WO 2013/034984 | 3/2013 |
| WO | WO 2013/034985 | 3/2013 |
| WO | WO 2013/057032 | 4/2013 |
| WO | WO 2013/057033 | 4/2013 |
| WO | WO 2013/057034 | 4/2013 |
| WO | WO 2014/005808 | 1/2014 |
| WO | WO 2014/033141 | 3/2014 |
| WO | WO 2014/066461 | 5/2014 |
| WO | WO 2014/139914 | 9/2014 |
| WO | WO 2014/139922 | 9/2014 |
| WO | WO 2014/146209 | 9/2014 |
| WO | WO 2014/164943 | 10/2014 |
| WO | WO 2015/004049 | 1/2015 |
| WO | WO 2015/004050 | 1/2015 |
| WO | WO 2015/019071 | 2/2015 |
| WO | WO 2015/062915 | 5/2015 |
| WO | WO 2016/001304 | 1/2016 |
| WO | WO 2016/193343 | 12/2016 |
| WO | WO 2016/193344 | 12/2016 |
| WO | WO 2016/193346 | 12/2016 |

(56) References Cited

OTHER PUBLICATIONS

U.S. Appl. No. 16/759,789, filed Apr. 28, 2020, Schader et al.
Karpova, "The basics of surdopedagogy", Ekaterinburg, pp. 20-21, 2008.
PCT International Preliminary Report on Patentability in International Appln. No. PCT/EP2016/062449, dated Dec. 5, 2017, 6 pages.
PCT International Preliminary Report on Patentability in International Appln. No. PCT/EP2016/062450, dated Dec. 5, 2017, 7 pages.
PCT International Preliminary Report on Patentability in International Appln. No. PCT/EP2016/062452, dated Dec. 5, 2017, 7 pages.
PCT International Preliminary Report on Patentability in International Appln. No. PCT/EP2016/062454, dated Dec. 5, 2017, 7 pages.
PCT International Preliminary Report on Patentability in International Appln. No. PCT/EP2018/079915, dated May 5, 2020, 8 pages.
PCT International Preliminary Report on Patentability in International Appln. No. PCT/EP2018/079917, dated May 5, 2020, 8 pages.
PCT International Search Report and Written Opinion in International Appln. No. PCT/EP2016/062449, dated Aug. 17, 2016, 8 pages.
PCT International Search Report and Written Opinion in International Appln. No. PCT/EP2016/062450, dated Aug. 5, 2016, 9 pages.
PCT International Search Report and Written Opinion in International Appln. No. PCT/EP2016/062452, dated Sep. 15, 2016, 11 pages.
PCT International Search Report and Written Opinion in International Appln. No. PCT/EP2016/062454, dated Aug. 5, 2016, 9 pages.
PCT International Search Report and Written Opinion in International Appln. No. PCT/EP2018/079915, dated Dec. 5, 2018, 13 pages.
PCT International Search Report and Written Opinion in International Appln. No. PCT/EP2018/079917, dated Dec. 5, 2018, 10 pages.
Engineers Edge, "Transducers USA Announced Improved TRIP60 Series of Audio Alerts", Engineering and Technology News, Aug. 2007, 3 pages.
National Standards of People's Republic of China, "Audible and/or Visual Fire Alarm Signaling Appliances", General Administration of Quality Supervision, Inspection and Quarantine of the People's Republic of China, Jul. 2011, 39 pages (with machine translation).
National Standards of People's Republic of China, "Fire Detection and Alarm Systems—Smoke Alarms", General Administration of Quality Supervision, Inspection and Quarantine of the People's Republic of China, Jul. 2006, 45 pages (with machine translation).
National Standards of People's Republic of China, "Vehicle Electronic Sirens", General Administration of Quality Supervision, Inspection and Quarantine of the People's Republic of China, Dec. 2014, 31 pages (with machine translation).

\* cited by examiner

DRUG DELIVERY DEVICE

CROSS REFERENCE TO RELATED APPLICATIONS

The present application is a continuation of U.S. patent application Ser. No. 15/578,567, filed on Nov. 30, 2017, which is the national stage entry of International Patent Application No. PCT/EP2016/062449, filed on Jun. 2, 2016, and claims priority to Application No. EP 15170581.1, filed in on Jun. 3, 2015, the disclosures of which are expressly incorporated herein in entirety by reference thereto.

TECHNICAL FIELD

The disclosure relates to a drug delivery device.

BACKGROUND

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by a plunger which is continuously pressed during the injection. There are numerous disadvantages associated with this approach. For example, if the plunger is released prematurely, the injection will stop and may not deliver an intended dose. Furthermore, the force required to push the plunger may be too high (e.g., if the user is elderly or a child). And, aligning the injection device, administering the injection, and keeping the injection device still during the injection may require dexterity which some patients may not have.

Autoinjector devices aim to make self-injection easier for patients. A conventional autoinjector may provide the force for administering the injection by a spring, and a trigger button or other mechanism may be used to activate the injection. Autoinjectors may be single-use or reusable devices.

Furthermore, it is necessary to administer the full dose in order to achieve full effectiveness of the medicament within the patient.

Thus, there remains a need for an improved drug delivery device.

SUMMARY

Certain aspects of the present disclosure relate to providing an improved drug delivery device.

According to the present disclosure, a drug delivery device, e. g. a manual injection device or an autoinjector, comprises:
- a plunger disposed within a case, wherein the plunger is slidable from a proximal position into a distal position within the case,
- an audible indicator that comprises a resilient element, wherein the resilient element is in a first configuration when the plunger is in the proximal position, wherein the resilient element is deflected radially outwards to a second configuration during movement of the plunger from the proximal position towards the distal position, and wherein the resilient element moves towards the second configuration towards the first configuration when the plunger moves towards or reaches the distal position, thereby generating an audible and tactile signal.

The provided drug delivery device is improved due to the audible indicator which can be used for indicating to a patient or user that the full dose of medicament was spent. Thereby, noise is generated due to a deflection of the resilient element.

In another exemplary embodiment, the resilient element may initially be in the second configuration.

In an exemplary embodiment, the resilient element is configured as a leaf spring comprising a proximal spring section coupled to a distal spring section.

The resilient element may be S-shaped which allows the resilient element to remain in a relaxed state until end of drug delivery. This enables less mechanical stress of the resilient element during storage and drug delivery.

The proximal spring section may be fixed to the case, e. g. by a snap connection, wherein the distal spring end is configured as a free end of the resilient element.

Furthermore, the distal spring section may be bent radially inwards towards the plunger with respect to the proximal spring section. The distal spring section may be representing a ramp section for an increased proximal plunger circumference.

In an exemplary embodiment, the distal spring section of the resilient element may comprise a hook that is bent radially outwards relative to the distal spring section. The hook constitutes a stop area adapted to impact on the plunger in order to generate the audible and tactile signal.

In a further exemplary embodiment, the resilient element is radially spaced from a distal plunger section.

The resilient element may comprise a single metal component for generating a recognizable audible signal.

Furthermore, the resilient element remains in the first configuration during medicament delivery until a proximal plunger section abuts the distal spring section.

When the proximal plunger section abuts the distal spring section, thereby reaching the distal spring end, the resilient element is allowed to relax radially inwards. As a result, the distal spring end hits an outer circumference of the proximal plunger section, thereby generating the audible signal.

In an exemplary embodiment, the drug delivery device is configured as an autoinjector that comprises the case adapted to hold a medicament container, a needle shroud telescopically coupled to the case, a shroud spring biasing the needle shroud distally relative to the case, and a drive spring biasing the plunger from the proximal position towards the distal position for delivering a medicament from the medicament container.

In a further exemplary embodiment, the case comprises a syringe support for supporting an axial position of the medicament container relative to the case, wherein the syringe support comprises at least two support arms. In particular, the support arms are configured with different lengths, wherein one support arm is longer than the other support arm.

The resilient element may be coupled to the syringe support in a manner extending distally from one of the support arms.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given herein below and the accompanying drawings which are given by way of illustration only, and thus, are not limitative of the present disclosure, and wherein.

Corresponding parts are marked with the same reference symbols in all figures.

DETAILED DESCRIPTION

Figure 1:
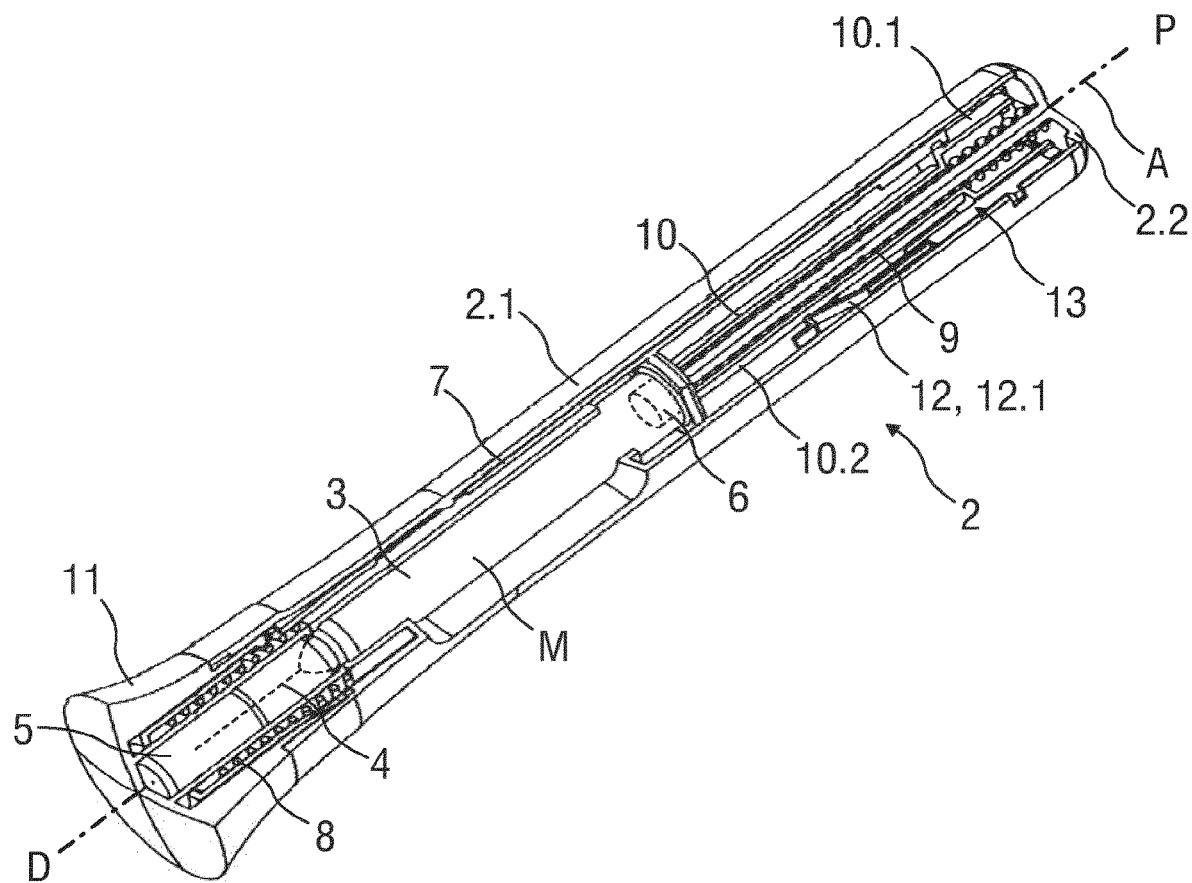
FIG. 1 is a schematic perspective partial section of an exemplary embodiment of a drug delivery device according to the present disclosure.

FIG. 1 shows a schematic perspective partial section of an exemplary embodiment of a drug delivery device 1 according to the present disclosure.

In the shown exemplary embodiment, the drug delivery device 1 is configured as an autoinjector device.

The drug delivery device 1 comprises a case 2 with a front case 2.1 and a rear case 2.2 and a longitudinal axis A extending from a proximal end towards a distal end. The case 2 is adapted to hold a medicament container 3, such as a syringe. The medicament container is referred to hereinafter as the "syringe 3". The syringe 3 may be a pre-filled syringe containing a medicament M and having a needle 4 arranged at a distal end of the syringe 3. In another exemplary embodiment, the medicament container 3 may be a cartridge which includes the medicament M and engages a removable needle (e.g. by threads, snaps, friction, etc.). In the shown exemplary embodiment, the syringe 3 is held in the case 2 and supported at its proximal end therein by a syringe support 13 that is further described in FIG. 3.

The drug delivery device 1 further comprises a protective needle sheath 5 that is coupled to the needle 4. For example, the protective needle sheath 5 is removably coupled to the needle 4. The protective needle sheath 5 may be a rubber needle sheath or a rigid needle sheath which is composed of rubber and a full or partial plastic shell.

For sealing the syringe 3 in a proximal direction P and for displacing a medicament M contained in the syringe 3 through the needle 4, a stopper 6 is provided and arranged within the syringe 3.

A needle shroud 7 is telescopically coupled to the case 2 and movable between a first extended position relative to the case 2 in which the needle 4 is covered and a retracted position relative to the case 2 in which the needle 4 is exposed. Furthermore, a shroud spring 8 is arranged to bias the needle shroud 7 distally against the case 2.

In the shown exemplary embodiment, a drive spring 9 is arranged within the case 2. A plunger 10 serves for forwarding a force of the drive spring 9 to the stopper 6. The plunger 10 is hollow and comprises a proximal plunger section 10.1 and a distal plunger section 10.2, wherein a diameter of the proximal plunger section 10.1 is larger than a diameter of the distal plunger section 10.2. The drive spring 9 is arranged within the plunger 10 biasing the plunger 10 distally against the case 2 as illustrated in FIG. 1. In another not shown exemplary embodiment, the plunger 10 may be solid and the drive spring 9 may engage a proximal end of the plunger 10.

Figure 5:
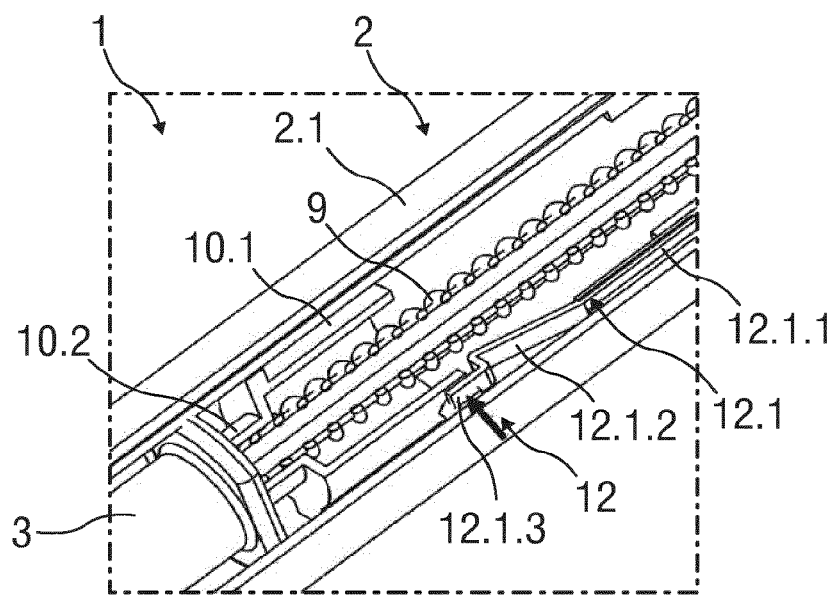
FIG. 5 is a schematic sectional view of the drug delivery device according to FIG. 1 with the plunger in the distal position.

The plunger 10 is movable from a proximal position (as illustrated in FIG. 1) towards a distal position (as illustrated in FIG. 5) relative to the case 2 to drive the medicament M from the syringe 3 through the needle 4 into the patient.

Furthermore, the plunger 10 may be prevented from releasing prior to retraction of the needle shroud 7 relative to the case 2. The plunger 10 may be configured to be released once the needle shroud 7 is sufficiently retracted. This is realized by a plunger release mechanism, which will not be described in more detail.

A cap 11 may be removably disposed at a distal end of the case 2, in particular at a distal end of the front case 2.1. The cap 11 may comprise grip features (not shown in detail) for facilitating a removal of the cap 11, e.g., by twisting and/or pulling the cap 11 off the case 2 and for engaging the protective needle sheath 5, the case 2 and/or the needle shroud 7. The grip features may include a barb, a hook, a narrowed section, etc.

As long as the cap 11 is in place, the needle shroud 7 is prevented from retracting relative to the case 2, thereby avoiding unintentional activation of the drug delivery device 1, e.g., if dropped, during shipping or packaging, etc. This is realized by a shroud lock mechanism, which will not be described in more detail.

The drug delivery device 1 further comprises at least one audible indicator 12 for producing an audible feedback for a user or patient indicating completion of medicament M delivery. In other words: The audible indicator 12 is provided to indicate to a user or a patient that the full dose of medicament M was spent.

According to the exemplary embodiment, the drug delivery device 1 comprises one audible indicator 12 that is arranged within the rear case 2.2.

The audible indicator 12 comprises a resilient element 12.1 and the proximal plunger section 10.1. The audible indicator 12 will be described in more detail within the description of the following FIGS. 2 to 5.

Figure 2:
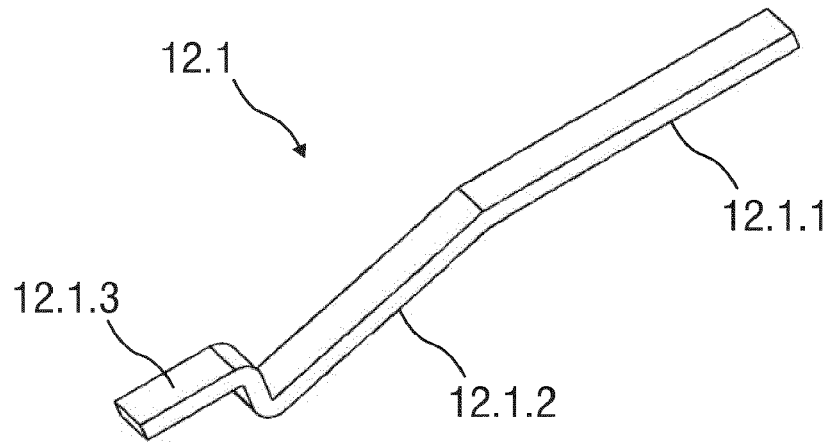
FIG. 2 is a schematic perspective view of an exemplary embodiment of a resilient element of the audible indicator.

FIG. 2 shows the resilient element 12.1 separately in a schematic perspective view.

According to the present embodiment, the resilient element 12.1 is configured as an S-shaped leaf spring comprising a proximal spring section 12.1.1 coupled to a distal spring section 12.1.2.

The distal spring section 12.1.2 is angled from the proximal spring section 12.1.1 representing a ramp section for the plunger 10 and comprises a distal spring end 12.1.3. The distal spring end 12.1.3 comprises a hook. The hook constitutes a stop area adapted to impact on an outer circumference of the plunger 10.

Furthermore, the resilient element 12.1 may comprise a single metal component. For example, the single metal component is coupled to the distal spring end 12.1.3.

Figure 3:
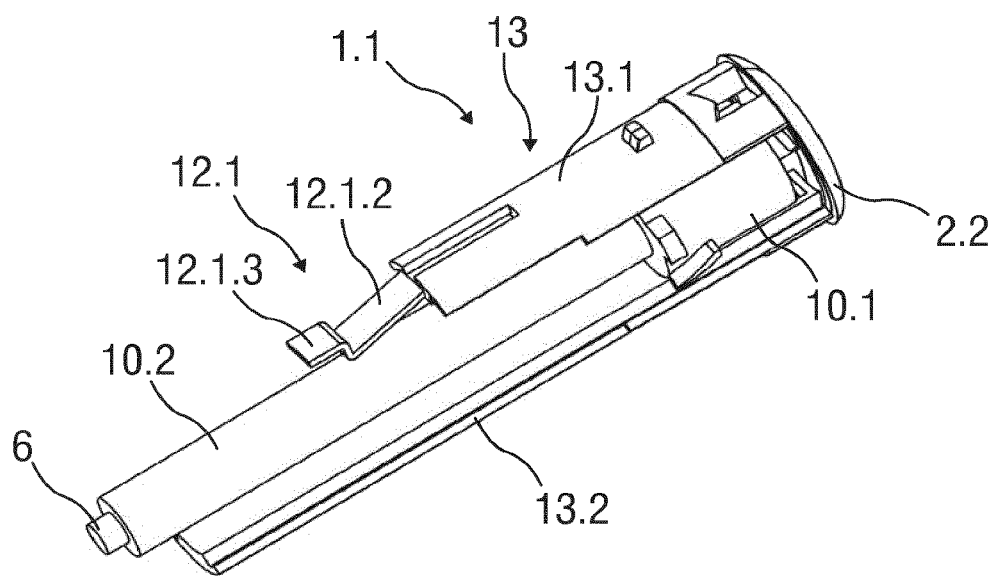
FIG. 3 is a schematic perspective view of an exemplary embodiment of a drive sub assembly of the drug delivery device comprising a rear case, a plunger and the audible indicator.

FIG. 3 shows the resilient element 12.1 assembled within a drive sub assembly 1.1 of the drug delivery device 1.

The drive sub assembly 1.1 is a sub assembly of the drug delivery device 1, wherein the drug delivery device 1 further comprises a front sub assembly (not shown separately) to allow for flexibility as to the time and location of manufacture of the subassemblies and final assembly with the syringe 3.

The rear case 2.2 comprises the syringe support 13 that is adapted to compensate variable lengths of the syringe 3 which occur due to manufacturing intolerances.

The syringe support 13 comprises two support arms 13.1, 13.2 that are arranged opposite to each other and that project in a distal direction D from a proximal end of the rear case 2.2. According to the present embodiment, the support arms 13.1, 13.2 are configured with different lengths regarding the longitudinal axis A. In particular, a first support arm 13.1 is shorter than a second arm 13.2 in order to create space for an arrangement of the resilient element 12.1.

In the shown embodiment, the resilient element 12.1 is coupled to the first support arm 13.1. In particular, the proximal spring section 12.1.1 is coupled to the first support arm 13.1. For example, the proximal spring section 12.1.1 is received within a guiding recess arranged on an inner side of the first support arm 13.1 and fixed by a snap connection.

Referring to the drug delivery device 1 illustrated in FIG. 1, the proximal spring section 12.1.1 may run in parallel to the longitudinal axis A. The proximal spring section 12.1.1 is furthermore radially spaced from an outer circumference of the distal plunger section 10.2 when assembled as illustrated in FIG. 3.

The distal spring section 12.1.2 projects distally from a free distal end of the first support arm 13.1 and is bent towards the outer circumference of the plunger 10 with respect to the proximal spring section 12.1.1. In the assembled state, the distal spring section 12.1.2 is radially spaced from the outer circumference of the distal plunger section 10.2 and angled from the longitudinal axis A in a radial inward direction.

As the proximal spring section 12.1.1 is fixed to the first support arm 13.1, the distal spring end 12.1.3 is configured as a free end of the resilient element 12.1. The hook arranged on the distal spring end 12.1.3 is bent radially outwards away from the outer circumference of the plunger 10. A free end of the hook runs in parallel to the longitudinal axis A in the assembled state of the resilient element 12.1.

To support the axial position of the syringe 3 relative to the case 2 after assembly, in particular during storage, transportation and normal use, the syringe support 13 may comprise one or more supporting beams (not shown) that are biased radially inwards to accommodate the variable length of the syringe 3 in an assembled state.

Figure 4:
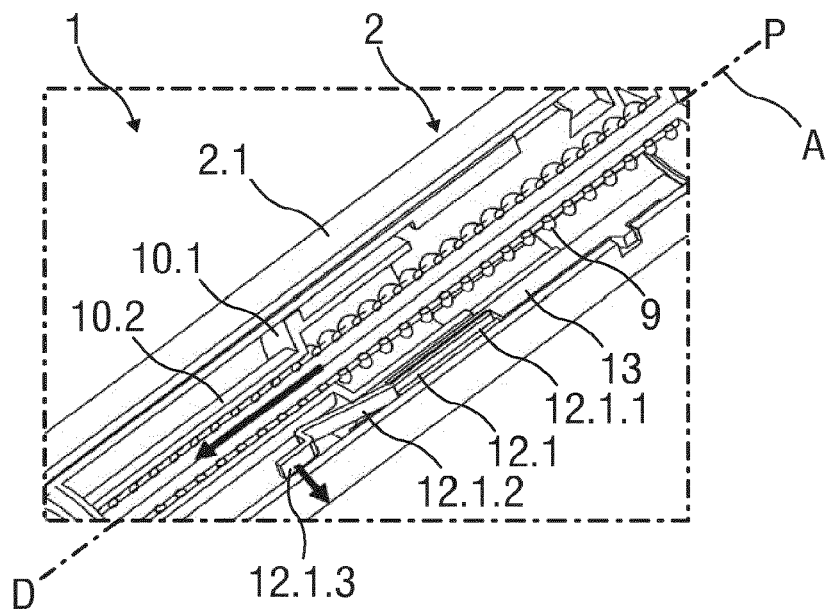
FIG. 4 is a schematic sectional view of a part of the drug delivery device according to FIG. 1 during movement of the plunger from a proximal position towards a distal position.

FIG. 4 shows an enlarged view of a section of the drug delivery device 1 as described in FIG. 1 during movement of the plunger 10 from the proximal position towards the distal position. The distal movement of the plunger 10 is indicated by an arrow illustrated within the plunger 10.

When the plunger 10 is in the proximal position, the resilient element 12.1 is in a first configuration which means in particular that the distal spring section 12.1.2 is in a relaxed state.

During movement of the plunger 10 from the proximal position towards the distal position, the distal spring section 12.1.2 is deflected radially outwards when the proximal plunger section 10.1 reaches the distal spring section 12.1.2. The distal spring section 12.1.2 is deflected radially outwards due to the increased diameter of the proximal plunger section 10.1. The deflection of the resilient element 12.1 is indicated by a further arrow pointing in a radial outward direction.

The distal spring section 12.1 is deflected until the proximal plunger section 10.1 passes the distal spring section 12.1.2 in the distal direction D as illustrated in FIG. 5.

FIG. 5 shows a schematic sectional view of the drug delivery device 1, wherein the plunger 10 is in the distal position.

Due to the radial outward bending of the distal spring end 12.1.3 away from the plunger 10, the resilient element 12.1 is allowed to move into a second configuration. In the second configuration, the biased distal spring section 12.1.2 relaxes radially inwards when the distal spring end 12.1.3 is still at the same level of the proximal plunger section 10.1 with respect to the longitudinal axis A. The distal spring end 12.1.3 hits an outer circumference of the proximal plunger section 10.1, thereby producing noise as an audible signal to indicate to a user that the full dose of medicament M was spent. The striking of the distal spring end 12.1.3 is indicated by an arrow pointing in the radial inward direction. The hitting noise generates an audible indication signal to a user that the full dose of medicament M was spent.

The skilled person readily understands that application of the audible indicator 12 is not limited to autoinjector devices. Instead, the audible indicator 12 may likewise be applied in a manually operated drug delivery device 1 for indicating that the plunger 10 has been completely moved into the distal position.

In an exemplary embodiment, when inserted in a drug delivery device 1, the resilient element 12.1 may produce an audible signal with a volume of at least 100 dB(A), e.g. measured at a distance of approximately 150 mm. In a test setup, the drug delivery device 1 was placed in a sound-absorbing environment on a table with the needle shroud 7 ahead. An elastomeric layer was located between the needle shroud 7 and the table to acoustically decouple the drug delivery device 1 from the table. Two microphones (e.g. ROGA MI-17 (IEPE)) were placed laterally from the drug delivery device 1 opposite each other at a distance of 150 mm, respectively and 170 mm above the table. A first test was performed with a user holding and operating the drug delivery device 1 with the right hand closed around the drug delivery device 1, wherein the fingers of the hand covered one side of the drug delivery device 1 directed towards one of the microphones and wherein the opposite side pointing towards the other microphone was covered by the palm of the hand. The volume of the audible signal on the finger side microphone was at least 100 dB(A) while the volume on the palm side microphone was lower than 100 dB(A). Another test was performed with a user holding and operating the drug delivery device 1 only with the fingertips of the right hand, wherein the palm of the hand was located between the drug delivery device 1 and one of the microphones; however, the drug delivery device 1 was not touched by the palm. The volume of the audible signal acquired by both microphones was at least 100 dB(A), wherein the volume detected by the palm side microphone was slightly lower than the volume detected by the other microphone.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')$_2$ fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 drug delivery device
2 case
2.1 front case
2.2 rear case
3 medicament container (syringe 3)
4 needle
5 protective needle sheath
6 stopper
7 needle shroud
8 shroud spring
9 drive spring
10 plunger
10.1 proximal plunger section
10.2 distal plunger section
11 cap
12 audible indicator
12.1 resilient element
12.1.1 proximal spring section
12.1.2 distal spring section
12.1.3 distal spring end
13 syringe support
13.1 first support arm
13.2 second support arm
D distal direction
M medicament
P proximal direction

The invention claimed is:

1. A drug delivery device comprising:
a plunger disposed within a case, wherein the plunger is configured to slide from a proximal position to a distal position within the case,
an audible indicator that comprises a resilient element, wherein the resilient element is configured to be in a radially outwards deflected state in a deflected configuration during movement of the plunger from the proximal position towards the distal position, and
the resilient element is configured to move from the deflected configuration towards a less deflected configuration when the plunger moves towards or reaches the distal position, thereby generating an audible signal,
wherein the resilient element is configured as a leaf spring comprising a proximal spring section coupled to a distal spring section,
wherein the drug delivery device comprises a longitudinal axis extending from a proximal end of the drug delivery device towards a distal end of the drug delivery device, and
wherein the proximal spring section extends parallel to the longitudinal axis of the drug delivery device when the resilient element is relaxed.

2. The drug delivery device according to claim 1, wherein the resilient element is fixed to the case, and wherein the distal spring section is configured as a free end of the resilient element.

3. The drug delivery device according to claim 1, wherein the audible indicator is configured to produce an audible feedback indicating completion of a medicament delivery.

4. The drug delivery device according to claim 1, wherein the resilient element is radially spaced from a distal plunger section.

5. The drug delivery device according to claim 1, wherein the resilient element comprises a single metal component.

6. The drug delivery device according to claim 1, wherein the resilient element moves towards the less deflected configuration when a proximal plunger section of the plunger passes the distal spring section of the resilient element.

7. The drug delivery device according to claim 1, wherein the drug delivery device is an autoinjector device comprising:
   the case adapted to hold a medicament container, and
   a drive spring biasing the plunger from the proximal position towards the distal position for delivering a medicament from the medicament container.

8. The drug delivery device according to claim 7, wherein the case comprises a syringe support for supporting an axial position of the medicament container relative to the case, wherein the syringe support comprises at least two support arms.

9. The drug delivery device according to claim 8, wherein the resilient element is coupled to a first one of the at least two support arms.

10. The drug delivery device according to claim 9, wherein a guiding recess is arranged on the first one of the at least two support arms, and wherein the resilient element is received within the guiding recess.

11. The drug delivery device according to claim 10, wherein the resilient element is received within the guiding recess by a snap connection.

12. The drug delivery device according to claim 7, comprising:
   a needle shroud telescopically coupled to the case, and
   a shroud spring biasing the needle shroud distally relative to the case.

13. The drug delivery device according to claim 7, wherein the medicament container is arranged within the case adjacent to an elongated drug window that allows a user of the autoinjector device to see the medicament of the medicament container.

14. The drug delivery device according to claim 13, wherein the medicament container is arranged within the case in physical contact with an edge of the elongated drug window.

15. The drug delivery device according to claim 1, wherein the resilient element is in the less deflected configuration when the plunger is in the proximal position.

16. The drug delivery device according to claim 1, wherein a side wall of the plunger is configured to be operatively coupled to a distal spring section of the resilient element in the deflected configuration.

17. The drug delivery device according to claim 1, wherein the plunger is configured to exert a force onto the resilient element which is directed radially outwards with regard to a longitudinal axis of the drug delivery device.

18. The drug delivery device according to claim 1, wherein in the deflected configuration, a lateral side wall of the plunger is configured to prevent potential energy stored within the resilient element from being released.

19. The drug delivery device according to claim 1,
   wherein the distal spring section is arranged at a first axial position relative to the longitudinal axis of the drug delivery device when the resilient element is relaxed,
   wherein the proximal spring section is arranged at a second axial position relative to the longitudinal axis of the drug delivery device when the resilient element is relaxed, and
   wherein the first axial position is different compared to the second axial position.

20. The drug delivery device according to claim 1, wherein the distal spring section extends parallel to the longitudinal axis of the drug delivery device when the resilient element is relaxed.

21. A drug delivery device comprising:
   a plunger disposed within a case adapted to hold a medicament container, wherein the plunger is configured to slide from a proximal position to a distal position within the case,
   a drive spring biasing the plunger from the proximal position towards the distal position for delivering a medicament from the medicament container,
   an audible indicator that comprises a resilient element, wherein the resilient element is configured to be in a radially outwards deflected state in a deflected configuration during movement of the plunger from the proximal position towards the distal position, and the resilient element is configured to move from the deflected configuration towards a less deflected configuration when the plunger moves towards or reaches the distal position, thereby generating an audible signal,
   wherein the case comprises a syringe support for supporting an axial position of the medicament container relative to the case, wherein the syringe support comprises at least two support arms,
   wherein the resilient element is coupled to a first one of the at least two support arms,
   wherein a guiding recess is arranged on the first one of the at least two support arms, and
   wherein the resilient element is received within the guiding recess.

22. A method of using a drug delivery device comprising:
   a plunger disposed within a case, wherein the plunger is configured to slide from a proximal position to a distal position within the case,
   an audible indicator that comprises a resilient element, wherein the resilient element is configured to be in a radially outwards deflected state in a deflected configuration during movement of the plunger from the proximal position towards the distal position, and
   the resilient element is configured to move from the deflected configuration towards a less deflected configuration when the plunger moves towards or reaches the distal position, thereby generating an audible signal,
   wherein the resilient element is configured as a leaf spring comprising a proximal spring section coupled to a distal spring section,
   wherein the drug delivery device comprises a longitudinal axis extending from a proximal end of the drug delivery device towards a distal end of the drug delivery device,
   wherein the proximal spring section extends parallel to the longitudinal axis of the drug delivery device when the resilient element is relaxed,
   wherein the method comprises delivering a drug using the drug delivery device.

* * * * *

UNITED STATES PATENT AND TRADEMARK OFFICE
CERTIFICATE OF CORRECTION

| | | |
|---|---|---|
| PATENT NO. | : 12,156,994 B2 | Page 1 of 1 |
| APPLICATION NO. | : 17/120670 | |
| DATED | : December 3, 2024 | |
| INVENTOR(S) | : Carsten Mosebach and Thomas Mark Kemp | |

It is certified that error appears in the above-identified patent and that said Letters Patent is hereby corrected as shown below:

In the Specification

In Column 1, Line 11 (approx.), before "on" delete "in"

Signed and Sealed this
Fourth Day of November, 2025

John A. Squires
*Director of the United States Patent and Trademark Office*